United States Patent
Perry et al.

(10) Patent No.: US 7,721,588 B2
(45) Date of Patent: May 25, 2010

(54) SYSTEMS AND METHODS FOR DETECTING PARTICLES

(75) Inventors: Kevin Joseph Perry, Pelham, NH (US); Matthew Edward Knapp, Marblehead, MA (US)

(73) Assignee: Morpho Detection, Inc., Newark, CA (US)

( * ) Notice: Subject to any disclaimer, the term of this patent is extended or adjusted under 35 U.S.C. 154(b) by 48 days.

(21) Appl. No.: 11/687,063

(22) Filed: Mar. 16, 2007

(65) Prior Publication Data

US 2007/0220953 A1      Sep. 27, 2007

Related U.S. Application Data

(60) Provisional application No. 60/784,413, filed on Mar. 21, 2006.

(51) Int. Cl.
*G01N 37/00*       (2006.01)

(52) U.S. Cl. .................. 73/28.01; 73/28.04; 73/863.21; 73/864.33

(58) Field of Classification Search ............... 73/28.01, 73/28.04, 863.21, 864.33, 864.81
See application file for complete search history.

(56) References Cited

U.S. PATENT DOCUMENTS

| | | | |
|---|---|---|---|
| 3,292,349 A | 12/1966 | Cuta | |
| 3,708,936 A | 1/1973 | Rogers | |
| 4,086,071 A | 4/1978 | Champlin | |
| 4,449,101 A | 5/1984 | Canzoneri et al. | |
| 4,909,089 A * | 3/1990 | Achter et al. | ............ 73/863.11 |
| 5,577,091 A | 11/1996 | Richardson et al. | |
| 5,836,861 A | 11/1998 | Diaz | |
| 5,861,950 A | 1/1999 | Knowlton | |
| 6,334,365 B1 | 1/2002 | Linker et al. | |
| 6,344,370 B1 | 2/2002 | Izumi et al. | |
| 6,503,758 B1 | 1/2003 | Allen et al. | |
| 6,610,977 B2 | 8/2003 | Megerle | |
| 6,708,572 B2 | 3/2004 | Jenkins et al. | |
| 6,840,122 B1 | 1/2005 | Jenkins et al. | |
| 6,972,408 B1 | 12/2005 | Reilly | |
| 6,978,657 B1 | 12/2005 | Baumann et al. | |

(Continued)

FOREIGN PATENT DOCUMENTS

EP          0955536    A2      10/1999

(Continued)

OTHER PUBLICATIONS

International Search Report for PCT/US2007/007004, Nov. 28, 2007.

*Primary Examiner*—Daniel S Larkin
(74) *Attorney, Agent, or Firm*—Armstrong Teasdale LLP

(57) ABSTRACT

A method of detecting particles during inspection is provided. The method includes establishing a security checkpoint including a detection system, wherein the detection system includes a chamber defining a passage and includes a plurality of jets. The method also includes passing an individual through the passage, enhancing a convection plume including particles from the individual by blowing air through at least one of the plurality of jets, and absorbing the particles in a preconcentrator including a filter encased in a frame having a high thermal conductivity. Moreover, the method includes evaporating the particles absorbed in the preconcentrator and using a detector to determine whether the particles are from at least one of an explosive material and a narcotic substance.

21 Claims, 5 Drawing Sheets

U.S. PATENT DOCUMENTS 7,141,786 B2 11/2006 McGann et al.
2006/0049346 A1 * 3/2006 McGann et al. ............. 250/287

FOREIGN PATENT DOCUMENTS

| GB | 1236093 A | 6/1971 |
| GB | 2265556 A | 6/1993 |
| GB | 2393403 A | 3/2004 |

* cited by examiner

SYSTEMS AND METHODS FOR DETECTING PARTICLES

CROSS REFERENCE TO RELATED APPLICATION

The present application relates to and claims priority from Provisional Application Ser. No. 60/784,413, filed Mar. 21, 2006, titled "SYSTEMS AND METHODS FOR DETECTING PARTICLES", the complete subject matter of which is hereby expressly incorporated by reference in its entirety.

BACKGROUND OF THE INVENTION

Embodiments of this invention relate generally to systems and methods for detecting particles, and more particularly, to systems and methods for detecting nanogram levels of particles.

Terrorism risks continue to exist at transportation facilities, government buildings and other high profile locations where there is a significant flow of pedestrian or vehicular traffic. As a result, most airports and many government buildings now include apparatus for detecting trace amounts of explosives. These devices typically operate on the principle that small amounts of the explosive materials will be transferred to the body, clothing and luggage of people who had handled the explosive. Generally, known trace portal systems use graded metal mesh for collecting samples. However, the graded metal mesh easily loses collection efficiency because it gets dirty and clogs easily.

Some detectors employ small flexible fabric-like traps that can be wiped across a package or piece of luggage. The trap removes residue from the surface of the package or luggage. The trap then is placed in an apparatus, such as an ion trap mobility spectrometer, that tests the residue on the trap for trace amounts of explosive materials. A device of this type is disclosed in U.S. Pat. No. 5,491,337 and is marketed by the GE Ion Track, Inc. of Wilmington, Mass. These devices typically are employed in proximity to metal detectors at airports, and security personnel will perform screening on some of the passengers based on a random sampling or based on a determination that the passenger has met certain criteria for enhanced screening.

The ion trap mobility spectrometer disclosed in U.S. Pat. No. 5,491,337 also can operate in a mode for detecting trace amounts of narcotics. Narcotics are illegal and insidious. Furthermore, it is known that many terrorists organizations fund their terrorism through the lucrative sale of narcotics.

Only a fraction of airline passengers have their carry-on baggage checked for trace amounts of explosives or narcotics using fabric-like traps and the available ion trap mobility spectrometers or similar devices. Efforts to use such devices to check all carry-on bags for trace amounts of explosives or narcotics would impose greater time and cost penalties on the airline industry. Additionally, the above-described explosive detectors typically are used only on luggage and other parcels. An apparatus of this type would not identify plastic explosives worn by a passenger who had no carry-on luggage. These related approaches provide low sensitivity and low throughput.

For the reasons stated above, and for other reasons discussed below, which will become apparent to those skilled in the art upon reading and understanding the present disclosure, there are needs unsolved by these related approaches to provide inspection devices having increased sensitivity to illegal substances carried by passengers, such as, but not limited to, narcotics and explosives, and devices having increased throughput.

BRIEF DESCRIPTION OF THE INVENTION

The above mentioned shortcomings, disadvantages and problems are addressed herein, which will be understood by reading and studying the following disclosure.

The embodiments described herein provide high sensitivity and high throughput. More specifically, the embodiments described herein provide a detector including a plurality of jets and a preconcentrator having a screen and a filter. The jets blow air on an individual to dislodge particles from the individual's clothes and skin, thus increasing a concentration of particles entrained in the individual's convention plume. The time required to evaporate particles from an individual's convection plume is decreased by increasing the effective area of the preconcentrator and surrounding the screen with a frame having high thermal conductivity. Thus, the embodiments described herein use a detector with high sensitivity and high throughput to quickly, accurately and efficiently identify illegal and insidious substances carried by passengers.

In one aspect, a method of detecting particles during inspection is provided. The method includes establishing a security checkpoint including a detection system, wherein the detection system includes a chamber defining a passage and includes a plurality of jets. The method also includes passing an individual through the passage, enhancing a convection plume including particles from the individual by blowing air through at least one of the plurality of jets, and absorbing the particles in a preconcentrator including a filter encased in a frame having a high thermal conductivity. Moreover, the method includes evaporating the particles absorbed in the preconcentrator and using a detector to determine whether the particles are from at least one of an explosive material and a narcotic substance.

In another aspect, a method of manufacturing a preconcentrator configured to decrease desorption time is provided. The method includes forming a frame having four sides that define an opening, positioning a filter over the opening in the frame, and bending each of the four sides of the frame about a corresponding side of the filter, wherein the frame has a high thermal conductivity.

In yet another aspect, a system for detecting particles is provided. The system includes a chamber, a plurality of jets, a preconcentrator, a detector, and a controller. The chamber includes a passage and the controller is configured to determine whether an individual is positioned within the passage. The plurality of jets is positioned within the chamber and configured such that at least one of the plurality of jets blows air on an individual within the passage to enhance a convection plume including particles from the individual. The preconcentrator includes a filter encased within a thermally conductive plate, wherein the filter is configured to absorb the particles and wherein the detector is configured to determine whether the particles are at least one of an explosive material and a narcotic substance.

In yet another aspect, an apparatus for detecting particles during inspection is provided. The apparatus includes a preconcentrator configured to decrease desorption time, wherein the preconcentrator comprises a filter encased by a thermally conductive frame.

DETAILED DESCRIPTION OF THE INVENTION

Figure 1:
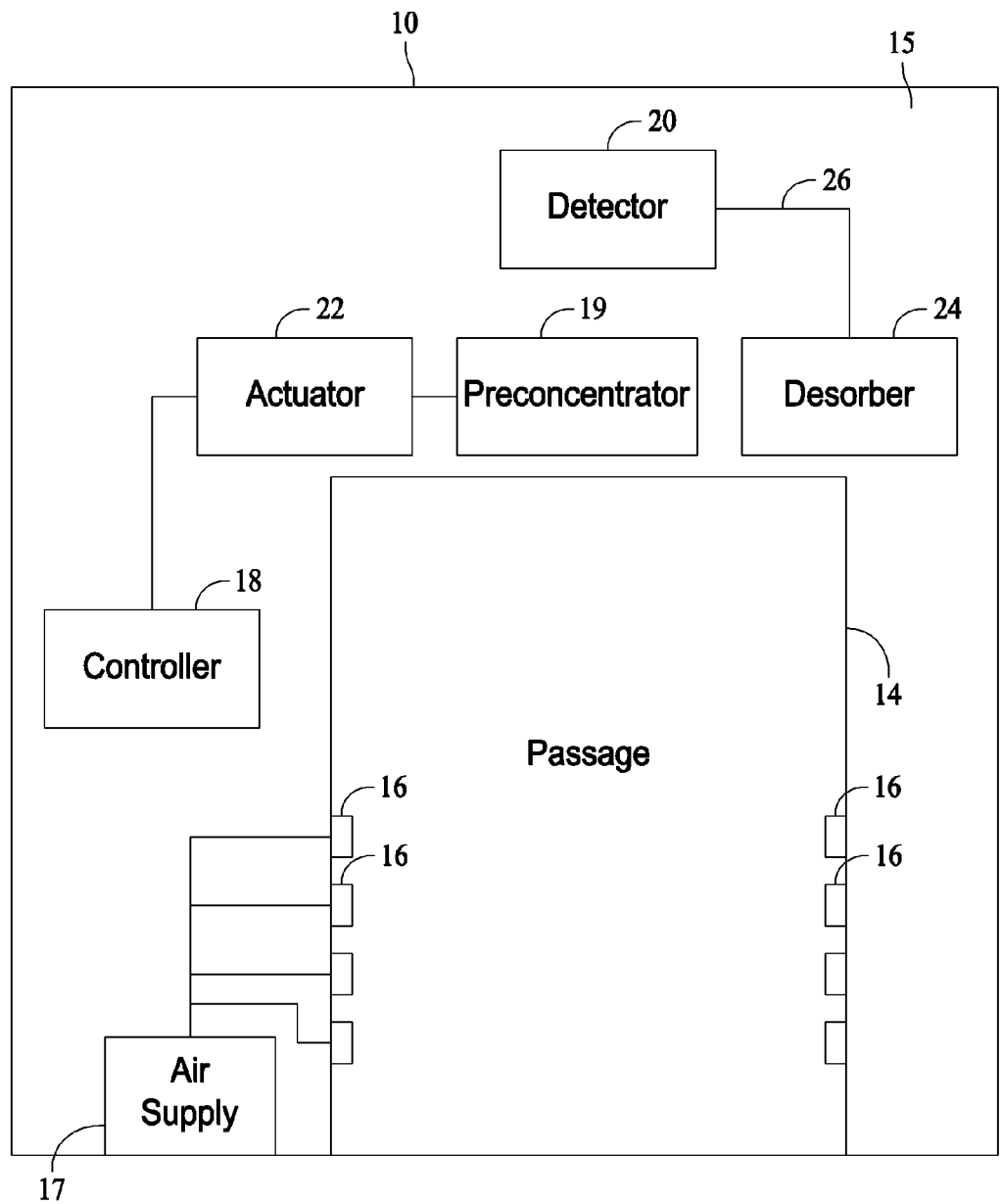
FIG. 1 is a schematic diagram of an embodiment of a detection system.

FIG. 1 is a schematic diagram of an embodiment of a detection system 10. The detection system 10 includes a passage 14 extending through detection system 10. The detection system 10 is installed at a security checkpoint and the passage 14 is dimensioned to conveniently accommodate a person who desires clearance at the security checkpoint. Detector 20 system 10 also includes a chamber 15.

A boundary layer of air adjacent to the person is heated by the person and generally is hotter than ambient air at farther distances from the person. Hot air is less dense than cooler air and rises relative to the more dense cooler air. As a result, a significant human convection plume of hot air rises in the boundary area adjacent to the person. The human convection plume generally achieves flow rates of 50-100 liters/second. This significant flow of the human convection plume tends to entrain a plurality of particles, such as particles of an explosive material or a narcotic substance, that are on the skin or clothing of the person passing through the passage 14. Thus, the microscopic particles travel upwardly with the human convection plume.

The detection system 10 includes a plurality of air jets 16 that direct short puffs of air towards the person in the passage 14. The jets 16 are directed at an area of the person extending roughly from the feet to the head and help to dislodge the particles from the skin and clothing of the person to stimulate separation of the particles from the skin and clothing, and to increase a concentration of the particles entrained in the human convection plume. The detection system 10 further includes a compressed air supply 17 that is controlled to fire the jets 16 sequentially from bottom to top as explained in U.S. Pat. No. 6,708,572. However, other jet firing patterns can be used.

The detection system 10 further includes a controller 18, a preconcentrator 19 and a detector 20. An example of detector 20 includes an ion trap mobility spectrometer as described in U.S. Pat. No. 5,491,337. Detection system 10 also includes an actuator 22, such as an electric motor, and a desorber 24. Controller 18, actuator 22, preconcentrator 19, desorber 24, and detector 20 are located within a chamber 15. Alternatively, controller 18, actuator 22, preconcentrator 19, desorber 24, and detector 20 are located outside chamber 15. As used herein, the term controller is not limited to just those integrated circuits referred to in the art as a controller, but broadly refers to computers, processors, microcontrollers, microcomputers, programmable logic controllers, application specific integrated circuits, and other programmable circuits, and these terms are used interchangeably herein. Actuator 22 is coupled to preconcentrator 19. Preconcentrator 19 receives the human convection plume including the particles from the person. Preconcentrator 19 absorbs or attracts the particles received. Controller 18 determines, such as from a change of an electromagnetic field within passage 14, whether the person is within passage 14. Upon determining that the person is within passage 14, controller 18 sends a controller output signal to drive actuator 22. Actuator 22 receives the controller output signal and drives preconcentrator 19 to move preconcentrator 19 inside desorber 24. Desorber 24, via a plurality of heating elements, generates heat that is supplied to preconcentrator 19. The particles absorbed by preconcentrator 19 are evaporated upon receiving the heat from desorber 24. Detector 20 receives, via a tube 26, the particles evaporated from desorber 24. Detector 20 detects whether particles are of illegal substances, such as narcotics or explosive substances. When the person moves out of the passage 14, controller 18 sends a signal to actuator 22 and actuator 22 retracts preconcentrator 19 from desorber 24. Preconcentrator 19 is outside desorber 24 when retracted from desorber 24.

Figure 2:
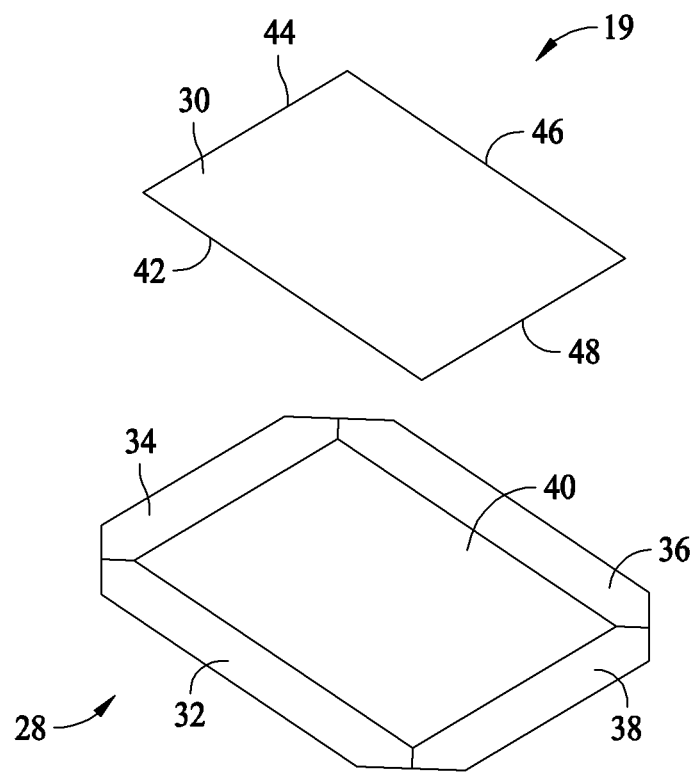
FIG. 2 is an isometric view of an embodiment of a preconcentrator of the detection system.

FIG. 2 is an isometric view of an embodiment of preconcentrator 19. More specifically, preconcentrator 19 includes a metal frame 28 encasing metal mesh or screen 30. Frame 28 is fabricated from a metal material, such as, but not limited to, aluminum, steel, and iron. Moreover, screen 30 is fabricated from a metal material, such as, but not limited to, aluminum, steel, and iron. Although the exemplary embodiment describes frame 28 as fabricated from a metal material, it should be appreciated that in other embodiments, frame 28 may be fabricated from any material of high thermal conductivity that enables detection system 10 to function as described herein. Frame 28 includes four sides 32, 34, 36, and 38 and an opening 40 is formed between the sides 32, 34, 36, and 38. Side 32 is adjacent to side 34, side 34 is adjacent to side 36, side 36 is adjacent to side 38, and side is 38 adjacent to side 32. Opening 40 is adjacent to sides 32, 34, 36, and 38. Frame 28 has the same shape as that of screen 30. In an alternative embodiment, frame 28 has more or less than four sides. As an example, frame 28 has three sides. As another example, frame 28 has five sides. In another alternative embodiment, screen 30 has more or less than four sides. As an example, screen 30 has three sides. As another example, screen 30 has six sides. In yet another alternative embodiment, frame 28 has another shape, such as square, triangular, hexagonal, or octagonal shape. In another alternative embodiment, screen 30 has another shape, such as square, triangular, hexagonal, or octagonal shape.

Figure 3:
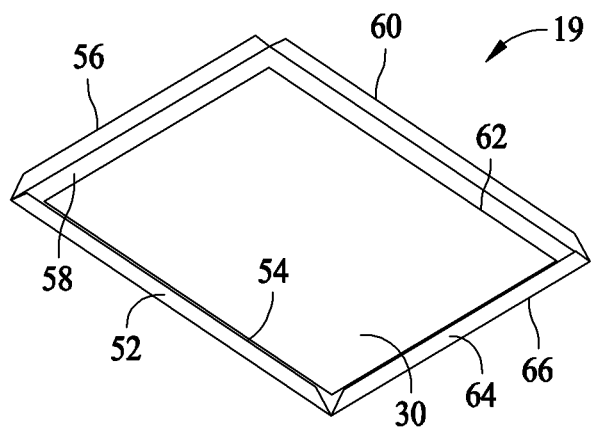
FIG. 3 is another isometric view of the preconcentrator.

FIG. 3 is an isometric view of an embodiment of preconcentrator 19. Screen 30 is placed so that a side 42 of screen 30 is adjacent to side 32, a side 44 of screen 30 is adjacent to side 34, a side 46 of screen 30 is adjacent to side 36, and a side 48 of screen 30 is adjacent to side 38. Each side of frame 28 is bent to form a plurality of portions of frame 28. For example, side 32 is bent to divide side 32 into portions 52 and 54. As another example, side 34 is bent to divide side 34 into portions 56 and 58. As yet another example, side 36 is bent to divide side 36 into portions 60 and 62. As still another example, side 38 is bent to divide side 38 into portions 64 and 66.

Figure 4:
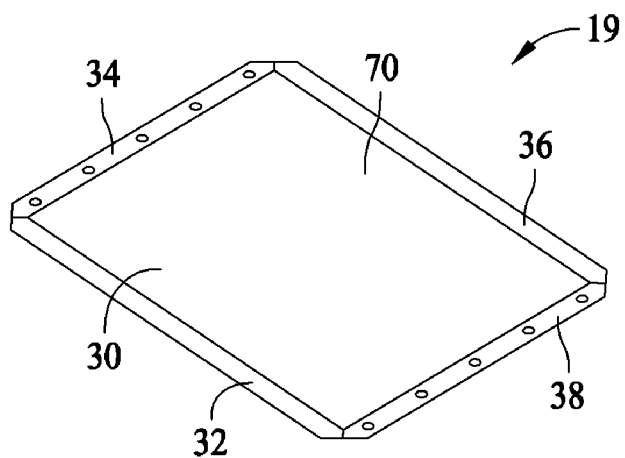
FIG. 4 is yet another isometric view of the preconcentrator.
Figure 5:
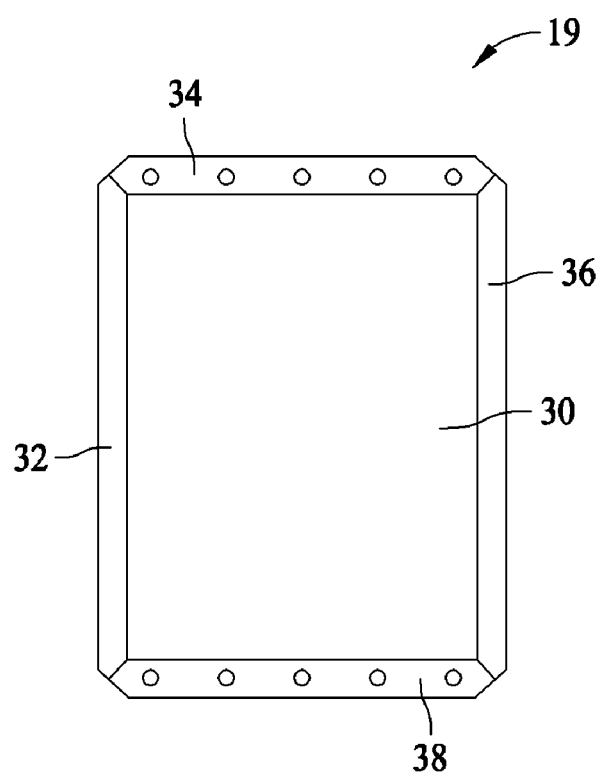
FIG. 5 shows a top view of the preconcentrator.
Figure 6:
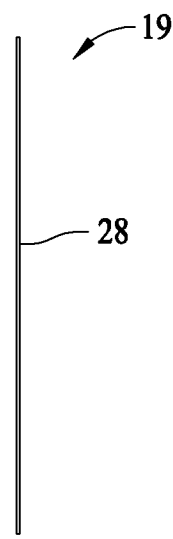
FIG. 6 shows a side view of the preconcentrator.

FIG. 4 is an isometric view of an embodiment of preconcentrator 19. Sides 32, 34, 36, and 38 are bent to fit screen 30 within frame 28. For example, side 32 is bent so that portion 52 is adjacent to a top face 70 of screen 30 and portion 56 is adjacent to a bottom face of screen 30. As another example, side 34 is bent so that portion 56 is adjacent to top face 70 of screen 30 and portion 58 is adjacent to bottom face of screen 30. As yet another example, side 36 is bent so that portion 60 is adjacent to top face 70 of screen 30 and portion 62 is adjacent to bottom face of screen 30. As still another example, side 38 is bent so that portion 64 is adjacent to top face 70 of screen 30 and portion 66 is adjacent to bottom face of screen 30. FIG. 5 shows a top view of an embodiment of preconcentrator 19 and FIG. 6 shows a side view of preconcentrator 19. When screen 30 is fitted within frame 28 and preconcentrator 19 is placed within desorber 24, the heat flows from desorber 24 to frame 28. The heat from frame 28 flows to screen 30.

Figure 7:
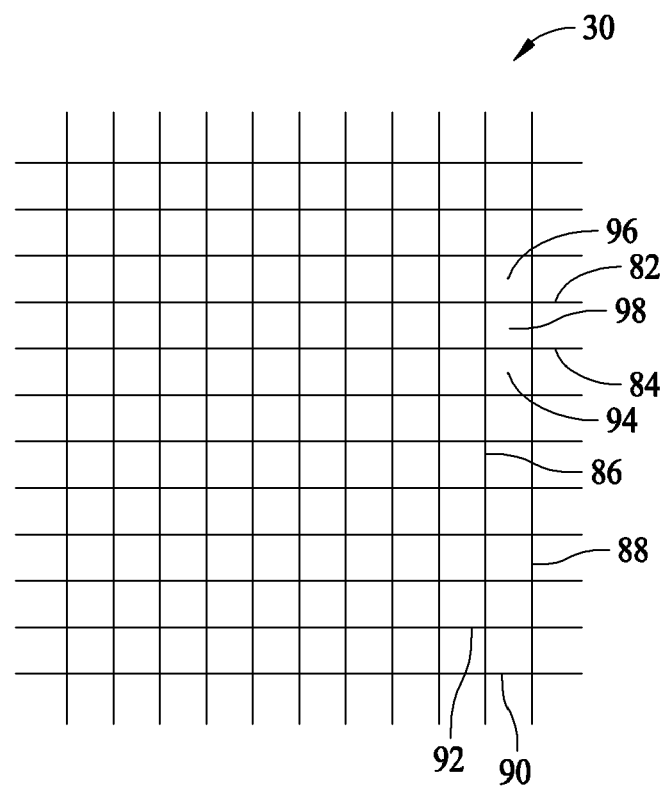
FIG. 7 is a schematic of an embodiment of a screen of the preconcentrator.

FIG. 7 is a schematic of an embodiment of screen 30. Screen 30 includes a mesh formed from a plurality of conducting mediums, such as conducting mediums 82, 84, 86, 88, 90, and 92, that are made of a metal, such as aluminum, steel, or iron, that conducts heat. An example of a conducting medium includes a wire. Screen 30 includes a plurality of openings, such as openings 94, 96, and 98, formed between a plurality of conducting mediums of screen 30. It should be appreciated that screen 30 may also be considered as a filter. For example, opening 98 is formed between conducting mediums 82, 84, 86, and 88. Examples of shapes of openings of screen 30 include square, rectangular, triangular, or hexagonal. When particles pass through screen 30, the particles are attached or absorbed to a conducting medium of screen 30. Each opening of screen 30 is designed so that one of the particles having a maximum dimension, such as a maximum length, from a plurality of dimensions of the one of the particles is attracted by a conducting medium surrounding the opening. As an example, a range of the maximum dimension includes a range from and including about 1 micron to about 100 microns. As another example, the maximum dimension is about 20 microns. Each conducting medium of screen 30 has the same thickness as another conducting medium of screen 30. In an alternative embodiment, a conducting medium of screen 30 has a different thickness than at least one other conducting medium of screen 30. An example of the thickness of a conducting medium includes a diameter of the conducting medium of screen 30.

It should be appreciated that although the exemplary embodiment describes screen 30 as fabricated from a mesh formed from a plurality of conducting mediums, in other embodiments, screen 30 may be fabricated from any material, such as a metal weave material, that enables detection system 10 to function as described herein.

Figure 8:
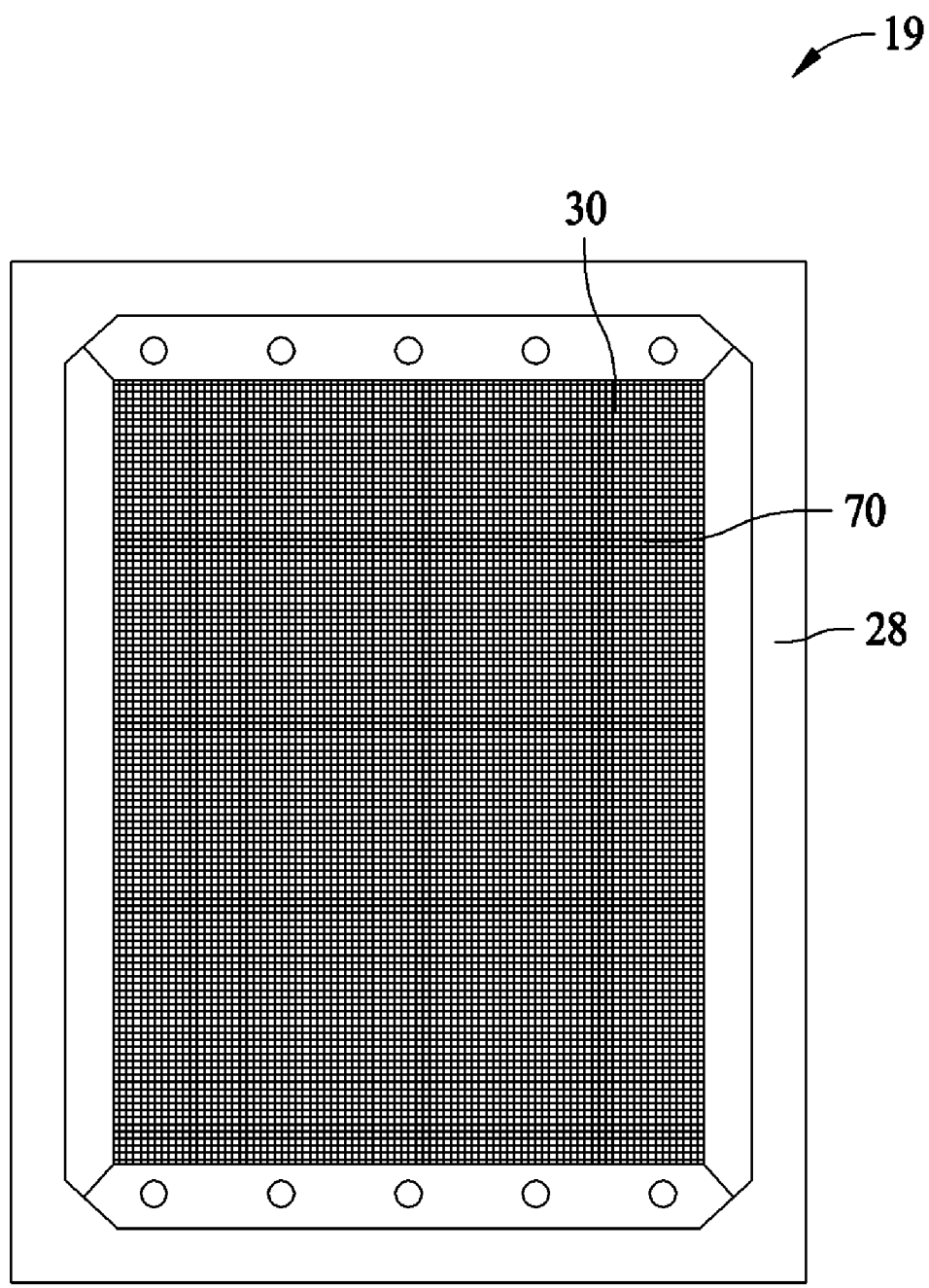
FIG. 8 is shows a top view of an embodiment of preconcentrator.

FIG. 8 is a top view of an embodiment of preconcentrator 19. Screen 30 is sintered into a uniform, non-graded pore structure. A flow of the human convection plume towards any side of preconcentrator 19 generates the same result. When preconcentrator 19 is inserted into desorber 24, the heat from desorber 24 flows from sides 32, 34, 36 and 38 to a center of preconcentrator 19. Screen 30 can be installed in any direction, such as, a direction in which top face 70 faces up away from a ground on which detection system 10 is placed or a direction in which top face 70 faces towards the ground. Preconcentrator 19 is thin and lighter than a typical preconcentrator. Tables 1 and 2, provided below, show a plurality of characteristics of various embodiments of preconcentrator 19. Although tables 1 and 2 describe characteristics of various embodiments of preconcentrator 19, it should be appreciated that in other embodiments, preconcentrator 19 may have any characteristic that enables detection system 10 to function as described herein.

TABLE 1

| Series | Abs. filter rating [μm] | Bubble point press. (1) [Pa] | Avg. air Perm. at 200 Pa. (2) [1/dm²/min] | Perm. factor K [m²] | H/K [1/m] | Thickness H [mm] | Wt [g/m²] | Porosity [%] | Dirt holding Capacity (3) [mg/cm²] |
|---|---|---|---|---|---|---|---|---|---|
| 3AL3 | 3 | 12300 | 9 | 4.80E−13 | 7.29E+08 | 0.35 | 975 | 65 | 6.40 |
| 5AL3 | 5 | 7600 | 34 | 1.76E−12 | 1.93E+08 | 0.34 | 600 | 78 | 5.47 |
| 7AL3 | 7 | 5045 | 57 | 2.35E−12 | 1.15E+08 | 0.27 | 600 | 72 | 6.47 |
| 10AL3 | 10 | 3700 | 100 | 4.88E−12 | 6.56E+07 | 0.32 | 600 | 77 | 7.56 |
| 15AL3 | 15 | 2470 | 175 | 9.87E−12 | 3.75E+07 | 0.37 | 600 | 80 | 7.92 |
| 20AL3 | 20 | 1850 | 255 | 1.91E−11 | 2.57E+07 | 0.49 | 750 | 81 | 12.44 |
| 25AL3 | 25 | 1480 | 320 | 2.98E−11 | 2.05E+07 | 0.61 | 1050 | 79 | 19.38 |
| 30AL3 | 30 | 1235 | 455 | 4.37E−11 | 1.44E+07 | 0.63 | 1050 | 79 | 23.07 |
| 40AL3 | 40 | 925 | 580 | 5.84E−11 | 1.13E+07 | 0.66 | 1200 | 77 | 25.96 |
| 60AL3 | 59 | 630 | 1000 | 1.07E−10 | 6.56E+06 | 0.70 | 750 | 87 | 33.97 |
| 5CL3 | 6 | 6100 | 35 | 4.38E−12 | 1.87E+08 | 0.82 | 975 | 85 | 11.67 |
| 10CL3 | 11 | 3500 | 95 | 1.07E−11 | 6.90E+07 | 0.74 | 900 | 85 | 17.13 |
| 15CL3 | 15 | 2400 | 200 | 2.29E−11 | 3.28E+07 | 0.75 | 900 | 85 | 18.95 |
| 20CL3 | 22 | 1700 | 325 | 3.67E−11 | 2.02E+07 | 0.74 | 900 | 85 | 29.10 |
| 5CL4 | 5 | 7400 | 27 | 1.65E−12 | 2.43E+08 | 0.40 | 900 | 72 | 6.80 |
| 7CL4 | 7 | 5286 | 45 | 2.74E−12 | 1.46E+08 | 0.40 | 900 | 72 | 9.50 |
| 10CL4 | 10 | 3700 | 71 | 4.33E−12 | 9.24E+07 | 0.40 | 900 | 72 | 9.50 |
| 15CL4 | 16 | 2400 | 150 | 9.15E−12 | 4.37E+07 | 0.40 | 900 | 72 | 11.90 |
| 20CL4 | 20 | 1850 | 200 | 1.22E−11 | 3.28E+07 | 0.40 | 900 | 72 | 12.00 |

TABLE 1-continued

| Series | Abs. filter rating [µm] | Bubble point press. (1) [Pa] | Avg. air Perm. at 200 Pa. (2) [1/dm²/min] | Perm. factor K [m²] | H/K [1/m] | Thickness H [mm] | Wt [g/m²] | Porosity [%] | Dirt holding Capacity (3) [mg/cm²] |
|---|---|---|---|---|---|---|---|---|---|
| 10FP3 | 11 | 3500 | 90 | 3.71E−12 | 7.29E+07 | 0.27 | 600 | 72 | 3.50 |
| 15FP3 | 15 | 2450 | 135 | 6.18E−12 | 4.86E+07 | 0.30 | 600 | 75 | 7.50 |
| 20FP3 | 21 | 1800 | 200 | 8.54E−12 | 3.28E+07 | 0.28 | 675 | 70 | 6.00 |
| 40FP3 | 40 | 925 | 540 | 2.39E−11 | 1.21E+07 | 0.28 | 675 | 71 | 9.00 |
| 5BL3 | 5 | 7000 | 45 | 1.17E−12 | 1.46E+08 | 0.17 | 300 | 78 | 4.00 |
| 10BL3 | 10 | 3700 | 100 | 2.59E−12 | 6.56E+07 | 0.17 | 300 | 78 | 4.63 |
| 15BL3 | 15 | 2470 | 175 | 4.54E−12 | 3.75E+07 | 0.17 | 300 | 78 | 4.70 |
| 20BL3 | 20 | 1850 | 255 | 6.61E−12 | 2.57E+07 | 0.17 | 300 | 78 | 6.10 |
| 40BL3 | 40 | 925 | 580 | 1.50E−11 | 1.13E+07 | 0.17 | 300 | 78 | 14.60 |
| 60BL3 | 59 | 650 | 1100 | 2.43E−11 | 5.96E+06 | 0.15 | 300 | 74 | 21.50 |

TABLE 2

| Series | Weight (g/m²) | Porosity % | Permeability At 200 Pa (1) (1/dm²/min) | DOP Efficiency [%] (2) 0.01 µm | 0.07 µm | 0.1 µm | 0.2 µm | 0.3 µm | 0.4 µm |
|---|---|---|---|---|---|---|---|---|---|
| 3AL3 | 975 | 65 | 9 | 99.995 | 97.656 | 96.679 | 96.805 | 98.747 | 99.484 |
| GA4 | 600 | 60 | 4 | 99.908 | 98.417 | 98.249 | 99.379 | 99.890 | 99.960 |
| GA5 | 900 | 60 | — | — | — | — | — | — | — |
| GA6 | 1200 | 60 | — | — | — | — | — | — | — |
| GA7 | 600 | 85 | 23 | 99.974 | 95.054 | 92.503 | 89.200 | 93.864 | 95.683 |
| GA8 | 1200 | 85 | 11 | 99.970 | 99.929 | 99.828 | 99.695 | 99.809 | 99.938 |
| GA9 | 2400 | 85 | 6 | 100.000 | 100.000 | 99.999 | 99.996 | 99.999 | 100.000 |
| GA10 | 600 | 85 | 96 | 99.939 | 65.498 | 59.296 | 42.319 | 57.351 | 58.777 |
| GA11 | 1200 | 85 | 85 | 99.996 | 94.161 | 90.398 | 81.438 | 86.874 | 89.044 |
| GA12 | 2400 | 85 | 16 | 99.994 | 99.640 | 99.111 | 97.393 | 98.311 | 98.824 |

Technical effects of the herein described systems and method for detecting the particles include reducing a time taken by desorber 24 to evaporate the particles attracted to preconcentrator 19 by an amount ranging from and including one second to three seconds compared to a typical time taken by desorber 24 to evaporate the particles. Another technical effect includes increasing an effective area of preconcentrator 19 from which the particles evaporate from and including 1.5 times to twice an effective area of a typical preconcentrator from which the particles evaporate. Other technical effects include surrounding screen 30 with frame 28 to facilitate improved evaporation of the particles.

While the invention has been described in terms of various specific embodiments, those skilled in the art will recognize that the invention can be practiced with modifications within the spirit and scope of the claims.

What is claimed is:

1. A method of detecting particles during inspection, said method comprising:
    absorbing particles from an individual in a preconcentrator comprising a filter encased in a frame configured to transfer heat to the filter to facilitate improved evaporation of the particles by conducting the heat from the frame to the filter, the filter having a thickness of less than 2 millimeters;
    evaporating the particles absorbed in the preconcentrator; and
    using a detector to determine whether the particles are from at least one of an explosive material and a narcotic substance.

2. A method in accordance with claim 1, wherein the frame has at least four sides that define an opening.

3. A method in accordance with claim 2, wherein the filter is one of a plurality of conducting mediums and a metal weave and wherein the filter is positioned in the opening of the frame and secured to the frame.

4. A method in accordance with claim 3, wherein at least one of each of the at least four sides of the frame is bent about a corresponding side of the filter.

5. A method in accordance with claim 1, wherein evaporating the particles from the preconcentrator further comprises:
    inserting the preconcentrator in a desorber; and
    applying heat to the preconcentrator.

6. A method in accordance with claim 1 wherein the frame facilitates the step of evaporating the particles and increases at least one of the detection system's sensitivity and throughput.

7. A method in accordance with claim 1, further comprising:
    establishing a security checkpoint including a detection system, the detection system comprising a chamber defining a passage and including a plurality of jets; and
    passing the individual through the passage and enhancing a convection plume including the particles from the individual by blowing air through at least one of the plurality of jets.

8. A method of manufacturing a preconcentrator configured to decrease desorption time, the method comprising:
    forming a substantially planar frame having sides that define an opening;

positioning a filter over the opening in the substantially planar frame, the filter having a thickness of less than 2 millimeters; and bending each of the sides of the substantially planar frame about a corresponding side of the filter, wherein the frame is configured to transfer heat to the filter to facilitate improved evaporation of particles on the filter by conducting the heat from the frame to the filter.

9. A method in accordance with claim 8 wherein the filter is one of a plurality of conducting mediums and a metal weave.

10. A method in accordance with claim 8 wherein the preconcentrator receives a convection plume.

11. A system for detecting particles, said system comprising:

a chamber comprising a passage;

a preconcentrator comprising a filter encased within a thermally conductive frame, said thermally conductive frame configured to facilitate improved evaporation of particles on said filter by conducting heat from said conductive frame to said filter, said filter having a thickness of less than 2 millimeters;

a detector;

a controller configured to determine whether an individual is positioned within said passage; and a plurality of jets positioned within said chamber and configured such that at least one of said plurality of jets blows air on the individual within said passage to enhance a convection plume including particles from the individual, said filter configured to absorb the particles and said detector configured to determine whether the particles are at least one of an explosive material and a narcotic substance.

12. A system in accordance with claim 11 wherein said filter comprises at least one of a plurality of conducting mediums and a metal weave.

13. A system in accordance with claim 11 further comprising a desorber configured to heat said preconcentrator and evaporate the particles to said detector.

14. A system in accordance with claim 11 wherein said preconcentrator is configured to receive the convection plume.

15. An apparatus for detecting particles during inspection, said apparatus comprising:

a preconcentrator configured to decrease desorption time, wherein the preconcentrator comprises:

a filter having a thickness of less than 2 millimeters; and a thermally conductive frame encasing said filter, said thermally conductive frame configured to facilitate improved evaporation of particles on said filter by conducting heat from said thermally conductive frame to said filter.

16. An apparatus in accordance with claim 15, wherein said filter is configured to collect particles from a convection plume associated with an individual.

17. An apparatus in accordance with claim 16, wherein the particles comprise at least one of an explosive material and a narcotic substance.

18. An apparatus in accordance with claim 15, wherein said preconcentrator is configured to operably couple to a desorber.

19. A apparatus in accordance with claim 15, wherein said thermally conductive frame comprises at least four sides that define an opening.

20. A apparatus in accordance with claim 19, wherein said filter comprises one of a plurality of conducting mediums and a metal weave, said filter positioned in said opening of said thermally conductive frame and secured to said thermally conductive frame.

21. A apparatus in accordance with claim 20, wherein said filter comprises at least four sides, at least one of each of the at least four sides of said thermally conductive frame is bent about a corresponding side of the at least four sides of said filter.

* * * * *